United States Patent [19]

Otake et al.

[11] Patent Number: 4,966,990
[45] Date of Patent: Oct. 30, 1990

[54] PROCESS FOR PRODUCING METHACRYLIC ACID AND/OR METHACRYLIC ACID ESTER

[75] Inventors: Masayuki Otake; Takashi Ushekubo, both of Yokohama, Japan

[73] Assignee: Mitsubishi Kasei Corporation, Tokyo, Japan

[21] Appl. No.: 314,257

[22] Filed: Feb. 24, 1989

Related U.S. Application Data

[63] Continuation of Ser. No. 469,700, Feb. 25, 1983, abandoned.

[30] Foreign Application Priority Data

Jul. 20, 1982 [JP] Japan ................. 57-126307

[51] Int. Cl.$^5$ ............................. C07C 67/30
[52] U.S. Cl. ................................. 560/214
[58] Field of Search ........................ 560/214

[56] References Cited

U.S. PATENT DOCUMENTS

| 4,320,227 | 3/1982 | Matsumoto et al. | 562/534 |
| 4,331,813 | 5/1982 | Daniel et al. | 560/214 |
| 4,335,258 | 6/1982 | Onoda et al. | 562/599 |

OTHER PUBLICATIONS

Mitsubishi Chem. Ind. Co., *Derwent Abstract*, 6419V/04 (J48-078,120), 20/10/73.
Mitsubishi Chem. Ind. KK, *Derwent Abstract*, 28061Y/16 (J52-031,108), 09/03/77.
Mitsubishi Chem. Ind. KK, *Derwent Abstract*, 73565Y/41 (J52-105,113), 03/09/77.
Mitsubishi Chem. Ind. KK, *Derwent Abstract*, 24466D/14 (J56-015,238), 14/02/81.
Mitsubishi Chem. Ind. KK, *Derwent Abstract*, 73564Y/41 (J52-105,112), 03/09/77.
Mitsubishi Chem. Ind. KK, *Derwent Abstract*, 40076W/24 (JP50-004,016), 16/01/75.
Mitsubishi Chem. Ind. KK, *Derwent Abstract*, 40077W/24 (J50-004,017), 16/01/75.

*Primary Examiner*—Paul J. Killos
*Attorney, Agent, or Firm*—Oblon, Spivak, McClelland, Maier and Neustadt

[57] ABSTRACT

A process for producing methacrylic acid and/or methacrylic acid ester by oxidative dehydrogenation of isobutyric acid and/or isobutyric acid ester, wherein the improvement comprises using a catalyst having the composition represented by

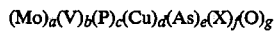

$$(Mo)_a(V)_b(P)_c(Cu)_d(As)_e(X)_f(O)_g$$

(where X denotes at least one element selected from the group consisting of lithium, beryllium, magnesium, barium, tin, lead, chromium, tungsten, and tellurium; subscripts a, b, c, d, e, f, and g each denote the ratio of the respective elements; b, c, d, e, and f are in the range of $0 \leq b \leq 3$, $0.2 \leq c \leq 2$, $0.005 \leq d \leq 2$, $0.005 \leq e \leq 0.2$, and $0.005 \leq f \leq 2$, respectively, when a is 12, and the value of g is determined according to the ratio and valence of the other elements), and at least a part of the composition having the heteropoly acid structure.

2 Claims, No Drawings

PROCESS FOR PRODUCING METHACRYLIC ACID AND/OR METHACRYLIC ACID ESTER

This application is a continuation of application Ser. No. 469,700, filed on Feb. 25, 1983, now abandoned.

BACKGROUND OF THE INVENTION

1. Field of the Invention

The present invention relates to a process for producing methacrylic acid or an ester thereof from isobutyric acid or an ester thereof.

2. Description of the Prior Art

It is known that methacrylic acid is formed when isobutyric acid undergoes oxidative dehydrogenation with molecular oxygen in the gas phase.

A catalyst containing molybdenum, vanadium, and phosphorus is effective for this reaction. Particularly effective is a heteropoly acid composed of molybdenum and vanadium for the condensation ligand atoms and phosphorus for the central atom. Such a catalyst exhibits high activity and high selectivity. (Japanese Patent Laid-open No. 78120/1973)

It is known that the catalyst is more improved in its performance by adding copper (Japanese Patent Laid-open No. 31018/1977), chromium (Japanese Patent Laid-open No. 105113/1977), lithium (Japanese Patent Laid-open No. 98131/1980), lead (Japanese Patent Laid-open No. 15238/1981), cadmium, uranium, indium, lanthanum, and cerium (Japanese Patent Laid-open No. 105112/1977), tellurium (Japanese Patent Laid-open No. 4016/1975), and thallium (Japanese Patent Laid-open No. 4017/1975). These catalysts are superior in activity and selectivity at beginning, but decrease in activity after use for a long period of time. Therefore, they are not satisfactory for industrial use.

It is known that a carbonyl compound, carboxylic acid, or ester having an isopropyl group at the α-position undergoes selective oxidative dehydrogenation with a heteropoly acid catalyst. The catalyst can be improved in activity and selectivity by adding a second component. The kind and quantity of the adequate second component vary depending on the type of the substrate.

Japanese Patent Laid-open No. 100324/1980 discloses catalysts of Mo-V-P-X-Y-O (where X is Cu, Sn, Th, Al, Ge, Ni, Fe, Co, Zn, Ti, Pb, Re, Zr, Ce, W, Bi, and As; and Y is K, Rb, Cs, and Tl) for producing methacrolein and methacrylic acid by oxidative dehydrogenation of isobutyraldehyde. Also, Japanese Patent Laid-open No. 100325/1980 discloses catalysts of Mo-V-P-Cu-X-Y-O (where X is As, Th, Al, Ge, Ni, Fe, Co, Zn, Ti, Pb, Re, Zr, Ce, W, Bi, Sn, and Cr; and Y is K, Rb, Cs, and Tl) for producing methacrolein and methacrylic acid from isobutyraldehyde in the same way.

However, in the case where the reaction substrate is isobutyric acid or an ester thereof, the effective additive is not the same; particularly, heavy alkalis such as K, Rb, and Cs greatly decrease the oxidative dehydrogenation and therefore are unfavorable for reaction.

Therefore, there is a continuing need for the catalyst having high activity, selectivity and long life.

SUMMARY OF THE INVENTION

The feature of this invention resides in using a catalyst having the composition represented by

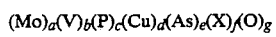

$$(Mo)_a(V)_b(P)_c(Cu)_d(As)_e(X)_f(O)_g \quad (I)$$

at least a part of the composition having the heteropoly acid structure, for producing methacrylic acid or methacrylic acid ester by oxidative dehydrogenation of isobutyric acid or isobutyric acid ester.

In the formula (I), Mo, V, P, Cu, As, and O represent molybdenum, vanadium, phosphorus, copper, arsenic, and oxygen, respectively; and X denotes at least one element selected from the group consisting of lithium, beryllium, magnesium, barium, tin, lead, chromium, tungsten, and tellurium. The subscripts a, b, c, d, e, f, and g each denote the ratio of the respective elements; b, c, d, e, and f are in the range of $0 \leq b \leq 3$ (preferably $0.5 \leq b \leq 3$), $0.2 \leq c \leq 2$, $0.005 \leq d \leq 2$, $0.005 \leq e \leq 0.2$, and $0.005 \leq f \leq 2$ (preferably $0.5 \leq f \leq 2$), respectively, when a is 12, and the value of g is determined according to the ratio and valence of the other elements.

The catalyst of this invention should be such that at least a part of it has the heteropoly acid structure.

DETAILED DESCRIPTION OF THE PREFERRED EMBODIMENTS

In the catalyst of this invention, the heteropoly acid structure includes heteropoly acid and a salt thereof. The presence of the heteropoly acid structure is confirmed by the X-ray diffraction pattern as shown in Table 1.

TABLE 1

| X-ray Diffraction Peaks of Heteropoly Acid Structure (Cu-Kα) |
|---|
| 2 θ (°) |
| 6.7 |
| 8.4 |
| 9.7 |
| 10.8 |
| 26.5 |

The raw materials for such catalysts are selected from the following compounds.

Molybdenum: Molybdenum trioxide, oxyacid of molybdenum, poly-acid thereof and salts thereof, heteropolymolybdic acid and salts thereof in which the central atom is phosphorus, silicon, or arsenic, and the ligand atom may be partly replaced by vanadium or tungsten.

Vanadium: Oxyacid such as vanadium pentoxide and metavanadium acid, poly-acid thereof and salts thereof, heteropolyvanadic acid and salts thereof in which the central atom is phosphorus, silicon, or arsenic, and the ligand atom may be partly replaced by molybdenum or tungsten.

Phosphorus: Oxyacid such as phosphorus pentoxide and orthophosphoric acid, poly-acid thereof and salts thereof, heteropolyphosphoric acid and salts thereof in which the coordination atom includes at least one of molybdenum, tungsten, and vanadium.

Copper: Copper oxide, copper carbonate, organic acid salt such as copper formate, inorganic acid salts such as copper phosphate, copper sulfate, copper nitrate, and copper chloride, and copper salt of heteropoly acid in which the central atom is phosphorus, silicon, or arsenic and the ligand atom is molybdenum, tungsten, or vanadium.

Arsenic: Oxyacid such as arsenic oxide and orthoarsenic acid, poly-acid thereof and salts thereof.

Beryllium, magnesium, barium, lead, and chromium: Oxides, carbonates, hydroxides, acetates and other organic acid salts, phosphates, sulfates, nitrates, chlorides and other inorganic acid salts, salt of heteropoly acid in which the central atom is phosphorus, silicon, or arsenic and the ligand atom is molybdenum, tungsten, or vanadium.

Tellurium: Oxyacid such as tellurium oxide and telluric acid and salts thereof, salt of heteropoly acid in which the coordination atom is tellurium and the ligand atom is molybdenum or vanadium.

Tungsten: Oxyacid such as tungsten trioxide and tungstic acid, poly-acid thereof and salts thereof, heteropolytungstic acid and salts thereof in which the coordination atom is phosphorus, silicon, or arsenic and the ligand atom may be partly replaced by molybdenum or vanadium.

Lithium: Lithium hydroxide and salts such as lithium carbonate, lithium nitrate, lithium chloride, lithium sulfate, and lithium acetate, lithium heteropolymolybdate in which the ligand atom may be partly replaced by vanadium and tungsten.

Tin: Stannic chloride, tin oxide, tin acetate, and other oxides and salts.

The catalyst can be produced by simply mixing the above-mentioned oxide, oxyacid, poly-acid, heteropolyacid, or salt thereof, or inorganic acid salt or organic acid salt. However, in the case where an oxyacid or oxide is used as the raw material of molybdenum, vanadium, arsenic, or phosphorus, it is preferable to heat them in an aqueous medium so that at least a part of it is dissolved. Dissolution promotes the formation of heteropoly acid. The aqueous medium for heating should preferably have a pH lower than 7. Using orthophosphoric acid as the raw material for phosphorus is most suitable.

According to the process of this invention, arsenic is used in an extremely small amount, and therefore it is considered that the heteropoly acid has mostly the condensation structure of 12-molybdophosphoric acid or similar compound composed of molybdenum, phosphorus and optional component vanadium.

The composition thus obtained can be made into a catalyst by the common method, e.g., supporting it on an inert carrier by impregnation or molding into granules of proper size after drying. Supporting by impregnation may be accomplished by supporting the optional component first and then supporting the other components. Carriers suitable for dipping method include, for example, silica, titania, diatomaceous earth, alumina, and silicon carbide. A high-silicious carrier having high water absorbability is preferable.

The reaction material used for the process of this invention is isobutyric acid or an isobutyric esters. The latter includes, for example, lower alkyl esters such as methyl ester and ethyl ester.

Usually, the reaction is performed under the condition that the molar ratio of oxygen to isobutyric acid or ester thereof is 0.1 to 10, preferably 0.5 to 5, the temperature is 200° to 500° C., the pressure is 0 to 30 kg/cm$^2$G, and the contact time is 0.01 to 20 seconds. The mixed material gas should preferably be diluted with inert component such as nitrogen, steam, or carbon dioxide. The reaction for isobutyric acid or an ester thereof is performed in a concentration range of 0.5 to 10 mol %. The waste gas resulting from oxidative dehydrogenation may be used, as such or after oxidation treatment, for the diluent gas.

The process of this invention is superior in the selectivity and yield of methacrylic acid or ester thereof. The catalyst containing lithium as X not only has high selectivity and yield but also keeps them for a long time of reaction.

Having generally described this invention, a more complete understanding can be obtained by examples which are provided herein for purposes of illustration only and are not intended to be limiting in any manner.

EXAMPLE 1

Preparation of catalyst

In a three-necked glass flask equipped with a reflux condenser were placed 100 g of aqueous solution containing 0.332 mmol/g of 10-molybdo-2-vanadophosphoric acid ($H_5Mo_{10}V_2PO_{40}$) and 0.164 g of arsenic oxide. The flask was heated under reflux with stirring for about 100 hours while blowing water-washed air. During the reaction, the liquid temperature was about 100° C. After cooling by standing, insoluble matters were filtered out, and the dark reddish filtrate was condensed to 75% concentration. This is called catalyst solution A.

The atomic composition of catalyst solution A is $Mo_{10}V_2P_1As_{0.05}$.

A carrier was pretreated by impregnating 13.7 g of spherically formed diatomaceous earth, 4 mm in average diameter, in 10 ml of aqueous solution containing 0.314 g of copper nitrate ($Cu(NO_3)_2 \cdot 3H_2O$), followed by drying and calcination. The pretreated carrier was impregnated in the above-mentioned catalyst solution A overnight, followed by separating the impregnated carrier from the solution and drying. Thus, there was obtained a catalyst.

EXAMPLE 2

Preparation of catalyst

In a 3-liter three-necked glass flask equipped with a reflux condenser were placed an aqueous slurry containing 270 g of molybdenum trioxide, 17.1 g of vanadium pentoxide, 21.6 g of orthophosphoric acid (85% aqueous solution), 3.0 g of copper (II) oxide, 1.9 g of arsenic oxide, and 2 liters of water. The flask was heated under reflux with stirring for about 100 hours while blowing water-washed air. During the reaction, the liquid temperature was about 100° C. After cooling by standing, insoluble matters were filtered out, and the dark reddish filtrate was condensed to 75% concentration. This is called catalyst solution B.

The atomic composition of catalyst solution B is $Mo_{10}V_1P_1Cu_{0.2}As_{0.05}$. On standing open at room temperature, the solution formed crystals.

The same diatomaceous earth carrier as used in Example 1 was impregnated in this solution overnight, followed by separating and drying. Thus, there was obtained a catalyst.

EXAMPLES 3 to 7

Preparation of catalysts

To the catalyst solution B obtained in Example 2 were added calculated quantities of magnesium carbonate, lead carbonate ($PbCO_3$), barium carbonate, tin oxalate, and telluric acid ($H_6TeO_6$). They were dissolved at room temperature.

Each of the resulting solutions were supported by impregnation on the same diatomaceous earth carrier as used in Example 1. Thus, there were obtained catalysts.

EXAMPLE 8

Preparation of catalyst

In a 500-ml three-necked glass flask equipped with a reflux condenser were placed an aqueous slurry containing 20 g of molybdenum trioxide, 1.26 g of vanadium pentoxide, 1.60 g of orthophosphoric acid (85% aqueous solution), 0.22 g of copper (II) oxide, 0.07 g of arsenic oxide ($As_2O_3$), 0.78 g of phosphotungstic acid, and 150 ml of water. The flask was heated under reflux with stirring for about 100 hours while blowing water-washed air. During the reaction, the liquid temperature was about 100° C. After cooling by standing, insoluble matters were filtered out, and the dark reddish filtrate was condensed to 75% concentration. This is called catalyst solution C. The atomic composition of this solution is $Mo_{10}V_1P_1W_{0.2}Cu_{0.2}As_{0.05}$.

The same diatomaceous earth carrier as used in Example 1 was impregnated in this solution overnight, followed by separating and drying. Thus, there was obtained a catalyst.

EXAMPLES 9 and 10

Preparation of catalysts

In a 1-liter three-necked glass flask equipped with a reflux condenser were placed an aqueous slurry containing 60 g of molybdenum trioxide, 3.79 g of vanadium pentoxide, 4.81 g of orthophosphoric acid (85% aqueous solution), 4.17 g of copper (II) oxide, 0.10 g of arsenic oxide ($As_2O_3$), and 600 ml of water. The flask was heated under reflux with stirring for about 100 hours while blowing water-washed air. During the reaction, the liquid temperature was about 100° C. After cooling by standing, insoluble matters were filtered out, and the dark reddish filtrate was condensed to 100 ml. This is called catalyst solution D. The atomic composition of this solution is $Mo_{10}V_1P_1Cu_{0.1}As_{0.025}$, and the concentration is 4.16 Mo-mg.atom/ml.

To the catalyst solution D was added calculated amounts of lithium carbonate, and dissolved at room temperature. The resulting solutions were supported by impregnation on the same diatomaceous earth carrier as used in Example 1. Thus, there was obtained catalysts 9 and 10.

EXAMPLE 11

Preparation of catalyst

In a 500-ml three-necked glass flask equipped with a reflux condenser were placed an aqueous slurry containing 30 g of molybdenum trioxide, 1.72 g of vanadium pentoxide, 2.18 g of orthophosphoric acid (85% aqueous solution), 0.30 g of copper (II) oxide, 0.30 g of arsenic oxide, 0.38 g of telluric acid, and 300 ml of water. The flask was heated under reflux with stirring for about 100 hours while blowing water-washed air. During the reaction, the liquid temperature was about 100° C. After cooling by standing, insoluble matters were filtered out, and the dark reddish filtrate was condensed to 75% concentration.

This is called catalyst solution E. The atomic composition of this solution is $Mo_{11}V_1P_1Cu_{0.2}As_{0.1}Te_{0.1}$.

The same diatomaceous earth carrier as used in Example 1 was impregnated in this solution overnight, followed by separating and drying. Thus, there was obtained a catalyst.

EXAMPLE 12

Preparation of catalyst

To the catalyst solution D obtained in Example 9 was added a calculated quantity of beryllium sulfate. The resulting solution was supported by impregnating on diatomaceous earth as in Example 9. Thus, there was obtained catalyst 12.

The catalysts obtained in the above examples gave X-ray diffraction patterns which are characteristic for the compound having the heteropoly acid structure as shown in Table 1.

EXAMPLE 13

Reaction

Into a stainless steel tubular reactor having an inner diameter of about 28.4 mm was charged the catalyst prepared in the above examples, and the reactor was heated by an electric furnace. A gas composed of isobutyric acid:steam:oxygen:nitrogen = 5:10:6.5:78.5 (molar ratio) was fed at a space velocity of 1800 hr$^{-1}$ (STP) to carry out reaction at 270° to 400° C. For some catalysts, the reaction was continued for 1000 to 2000 hours. The results are shown in Table 2.

TABLE 2

| Catalyst (Example) No. | Composition of catalyst (Atomic ratio) | Time elapsed (hr.) | Reaction temperature (°C.) | Conversion of isobutyric acid (%) | Selectivity to methacrylic acid (%) | Yield of methacrylic acid (%) |
|---|---|---|---|---|---|---|
| 1 | $Mo_{10}V_2P_1Cu_{0.2}As_{0.05}$ | 5 | 352 | 96.0 | 69.2 | 66.4 |
| 2 | $Mo_{10}V_1P_1Cu_{0.2}As_{0.05}$ | 5 | 333.5 | 96.0 | 73.3 | 70.4 |
|   |   | 1700 | 358.5 | 96.0 | 70.3 | 67.5 |
| 3 | $Mo_{10}V_1P_1Mg_{0.05}Cu_{0.2}As_{0.05}$ | 5 | 350 | 96.0 | 69.5 | 66.7 |
| 4 | $Mo_{10}V_1P_1Pb_{0.2}Cu_{0.2}As_{0.05}$ | 5 | 338.5 | 96.0 | 67.5 | 64.8 |
| 5 | $Mo_{10}V_1P_1Ba_{0.2}Cu_{0.2}As_{0.05}$ | 5 | 344 | 96.0 | 68.0 | 65.3 |
| 6 | $Mo_{10}V_1P_1Sn_{0.2}Cu_{0.2}As_{0.05}$ | 5 | 353.5 | 96.0 | 67.8 | 65.1 |
| 7 | $Mo_{10}V_1P_1Te_{0.2}Cu_{0.2}As_{0.05}$ | 5 | 346 | 96.0 | 70.0 | 67.2 |
| 8 | $Mo_{10}V_1P_1W_{0.2}Cu_{0.2}As_{0.05}$ | 5 | 338 | 96.0 | 72.2 | 69.3 |
|   |   | 1000 | 365 | 96.0 | 70.0 | 67.2 |
| 9 | $Mo_{10}V_1P_1Li_{0.1}Cu_{0.1}As_{0.025}$ | 5 | 335 | 96.0 | 72.0 | 69.1 |
|   |   | 1350 | 355 | 96.0 | 72.5 | 69.6 |
| 10 | $Mo_{10}V_1P_1Li_{0.5}Cu_{0.1}As_{0.025}$ | 5 | 357 | 96.0 | 70.6 | 67.8 |
| 11 | $Mo_{11}V_1P_1Cu_{0.2}As_{0.1}Te_{0.1}$ | 5 | 368 | 96.0 | 74.6 | 71.6 |
| 12 | $Mo_{10}V_1P_1Cu_{0.1}As_{0.025}Be_{0.05}$ | 5 | 337 | 96.0 | 73.8 | 70.8 |

EXAMPLE 14

Reaction

Oxidative dehydrogenation of methyl isobutyrate was carried out using the catalysts obtained in Examples 2 and 9.

Into a stainless steel tubular reactor having an inner diameter of about 28.4 mm was charged the catalyst, and the reactor was heated by an electric furnace. A material gas composed of methyl isobutyrate:oxygen:nitrogen=5:6.5:88.5 (molar ratio) was passed through the reactor at a space velocity of 1800 $hr^{-1}$ (STP) to carry out reaction at 270° to 400° C. The results are shown in Table 3.

TABLE 3

| Catalyst (Example) No. | Reaction temperature (°C.) | Yield of methyl methacrylate (%) | Yield of methacrylic acid (%) | Yield of methyl methacrylate + methacrylic acid (%) |
|---|---|---|---|---|
| 2 | 383.5 | 46.0 | 35.3 | 81.3 |
| 9 | 380.0 | 46.5 | 36.0 | 82.5 |

Having now fully described the invention, it will be apparent to one of ordinary skill in the art that many changes and modifications can be made thereto without departing from the spirit of the invention as set forth herein.

What is claimed as new and intended to be covered by Letters Patent is:

1. A process for producing methacrylic acid and/or methacrylic acid ester by the oxidative dehydrogenation of isobutyric acid and/or isobutyric acid ester, comprising: reacting said isobutyric acid and/or isobutyric acid ester in the vapor phase in the presence of oxygen over a catalyst having the formula: $(MO)_{12}(V)_b(P)_c(Cu)_d(As)_e(X)_f(O)_g$ wherein X denotes at least one element selected from the group consisting of lithium, beryllium, magnesium, tungsten and tellurium; subscripts b, c, d, e, f and g each denoting the atomic ratio of the representative elements and having the values: $0.5 \leq b \leq 3$, $0.2 \leq c \leq 2$, $0.005 \leq d \leq 2$, $0.005 \leq e \leq 0.2$ and $0.06 \leq f \leq 2$; and the value of g is determined by the ratio and valences of the other elements in the catalyst, at least a part of the catalyst having the heteropoly acid structure.

2. The process according to claim 1, wherein X is lithium.

* * * * *